United States Patent
Majeed et al.

(10) Patent No.: US 10,668,115 B2
(45) Date of Patent: Jun. 2, 2020

(54) **STABLE PROBIOTIC COMPOSITION CONTAINING *BACILLUS COAGULANS* MTCC 5856 AND METHOD OF DETECTION THEREOF**

(71) Applicants: Muhammed Majeed, Edison, NJ (US); Kalyanam Nagabhushanam, East Windsor, NJ (US); Shaheen Majeed, Springville, UT (US); Lakshmi Mundkur, Bangalore (IN)

(72) Inventors: Muhammed Majeed, Edison, NJ (US); Kalyanam Nagabhushanam, East Windsor, NJ (US); Shaheen Majeed, Springville, UT (US); Lakshmi Mundkur, Bangalore (IN)

(73) Assignee: SAMI LABS LIMITED, Bangalore (IN)

( * ) Notice: Subject to any disclaimer, the term of this patent is extended or adjusted under 35 U.S.C. 154(b) by 142 days.

(21) Appl. No.: 15/805,394

(22) Filed: Nov. 7, 2017

(65) Prior Publication Data

US 2018/0318362 A1 Nov. 8, 2018

Related U.S. Application Data

(60) Provisional application No. 62/426,265, filed on Nov. 24, 2016.

(51) Int. Cl.
| | |
|---|---|
| *G01N 15/14* | (2006.01) |
| *A61K 35/742* | (2015.01) |
| *C12N 1/20* | (2006.01) |
| *G01N 1/30* | (2006.01) |
| *C12Q 1/02* | (2006.01) |
| *C12N 1/04* | (2006.01) |
| *A61K 35/741* | (2015.01) |
| *A61K 35/745* | (2015.01) |
| *A61K 35/747* | (2015.01) |
| *C12Q 1/06* | (2006.01) |
| *G01N 15/10* | (2006.01) |

(52) U.S. Cl.
CPC .......... *A61K 35/742* (2013.01); *A61K 35/741* (2013.01); *A61K 35/745* (2013.01); *A61K 35/747* (2013.01); *C12N 1/04* (2013.01); *C12N 1/20* (2013.01); *C12Q 1/02* (2013.01); *C12Q 1/06* (2013.01); *G01N 1/30* (2013.01); *G01N 15/14* (2013.01); *G01N 15/1404* (2013.01); *G01N 2015/1006* (2013.01); *G01N 2015/1402* (2013.01); *G01N 2015/1486* (2013.01); *G01N 2015/1488* (2013.01)

(58) Field of Classification Search
None
See application file for complete search history.

(56) References Cited

PUBLICATIONS

Cronin et al., Cytometry Part A 71A: 143-153 (2007).*

\* cited by examiner

*Primary Examiner* — Erin M. Bowers

(57) ABSTRACT

Disclosed is a stable probiotic composition containing *Bacillus coagulans* MTCC 5856 exhibiting increased viability over wide range of pH and the use of flow cytometry method to enumerate the viable count of *Bacillus coagulans* MTCC 5856 under various environmental conditions.

2 Claims, 19 Drawing Sheets
(16 of 19 Drawing Sheet(s) Filed in Color)

Unstained

SYTO ™ BC

Stained

SYTO ™ BC

Unstained

CFDA

Stained

$10^7$/ml

$10^6$/ml

10⁵/ml

Spores

SYTO BC™

CFDA

Vegetative cells

SYTO BC™

CFDA

Spores + Live cells

SYTO BC™

Spores + killed cells(1:1)

24hrs
pH 2.0

Capsule

Tablet

Juice A

Juice B

Probiotic -A

Probiotic -B

Probiotic -C

Probiotic -D

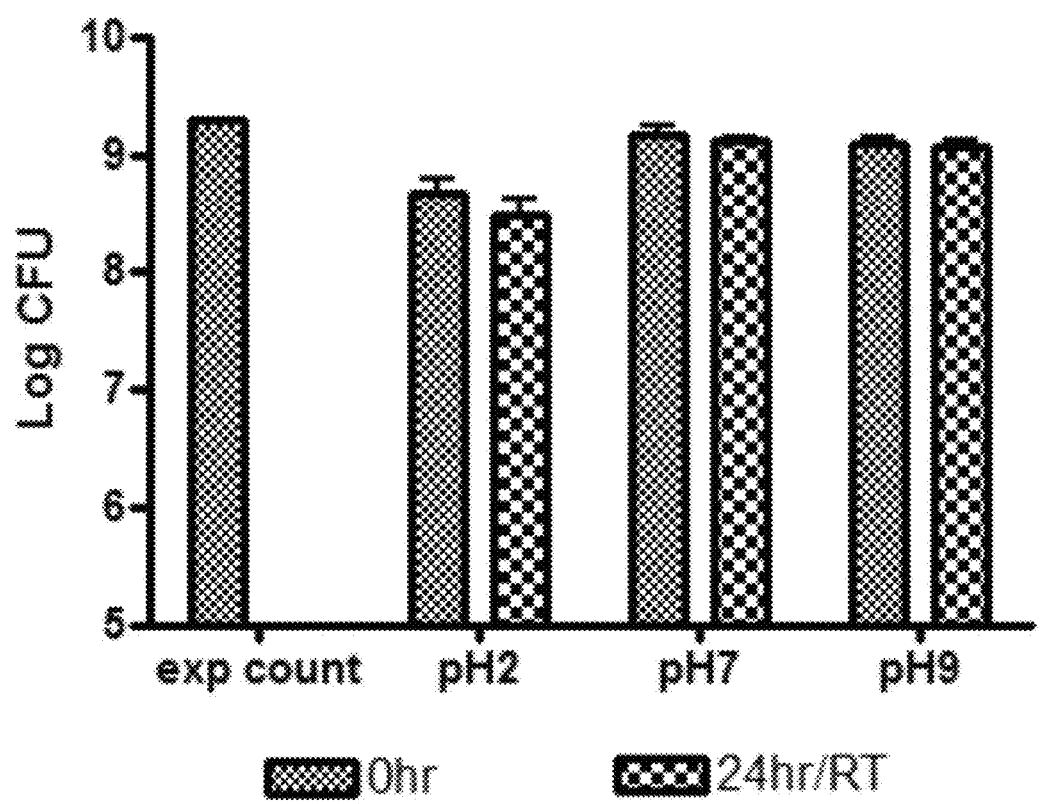

STABLE PROBIOTIC COMPOSITION CONTAINING *BACILLUS COAGULANS* MTCC 5856 AND METHOD OF DETECTION THEREOF

CROSS-REFERENCE TO RELATED PATENT APPLICATION

This is a non-provisional patent application claiming priority from U.S. Provisional Patent Application No. 62/426,265 filed on 24 Nov. 2016.

FIELD OF THE INVENTION

The present invention in general relates to stable probiotic composition containing *Bacillus coagulans* MTCC 5856 exhibiting increased viability over wide range of pH. More specifically the invention relates to the use of flow cytometry as a method to enumerate the viable count of *Bacillus coagulans* MTCC 5856 under various environmental conditions.

BACKGROUND OF THE INVENTION

Probiotics are now garnering attention as a dietary supplement owing to its medicinal and therapeutic benefits. It has shown exponential growth in the last decade and is now available in different formulations, and as probiotic enriched food and beverages. Viability is considered as an important aspect for the function of probiotics. A shelf stable, viable probiotic would always have a commercial edge over the others available in the market. Also, accurate enumeration of viable count of probiotic is important for its therapeutic activity. Probiotics are known to exist in a viable but non culturable state wherein, the standard plate count method of enumeration will not able to enumerate the spore count accurately. Several alternate methods can be used to determine the viable bacterial count which includes fluorescent in situ hybridization (FISH), polymerase chain reactions and microplate fluorochrome assay. (Enumeration of probiotic strains: Review of culture-dependent and alternative techniques to quantify viable bacteria, Catherine Davis, Journal of Microbiological Methods, Volume 103, August 2014, Pages 9-17).

The plate count method does not support precise, reproducible estimations of cell densities of probiotic strains, especially in mixed cultures (Suitability of MRS-bile agar for the selective enumeration of mixed probiotic bacteria in presence of mesophilic lactic acid cultures and yoghurt bacteria, S. Sohrabvandi, A.-M. Mortazavian, M.-R. Dolatkhnejad, A. B. Monfared, Iranian Journal of Biotechnology., 10 (2014 pp, 16-20. It estimates only the subset of viable organisms that replicate under the conditions of culture.

Hence it is necessary to develop a new method to determine the actual bacterial count of probiotic formulation. The present invention solves the above mentioned problems by disclosing a stable probiotic composition and its method of detection.

It is principle objective of the present invention to disclose a stable probiotic composition containing *Bacillus coagulants* MTCC 5856 exhibiting increased viability and stability over wide range of pH compared to other commercially available probiotics.

It is yet another objective of the present invention to disclose a simple, accurate, commercially viable flow cytometric method to detect and enumerate live spores and vegetative cells.

The present invention fulfils the aforesaid objectives and provides further related advantages.

SUMMARY OF THE INVENTION

Disclosed is stable probiotic composition containing *Bacillus coagulans* MTCC 5856 exhibiting increased viability over wide range of pH r and the use of flow cytometry method to enumerate the viable count of *Bacillus coagulans* MTCC 5856 under various environmental conditions.

Other features and advantages of the present invention will become apparent from the following more detailed description, taken in conjunction with the accompanying images, which illustrate, by way of example, the principle of the invention.

BRIEF DESCRIPTION OF DRAWINGS

The patent or application file contains at least one drawing executed in color. Copies of this patent or patent application publication with color drawing(s) will be provided by the office upon request and payment of the necessary fee.

Figure 1A:
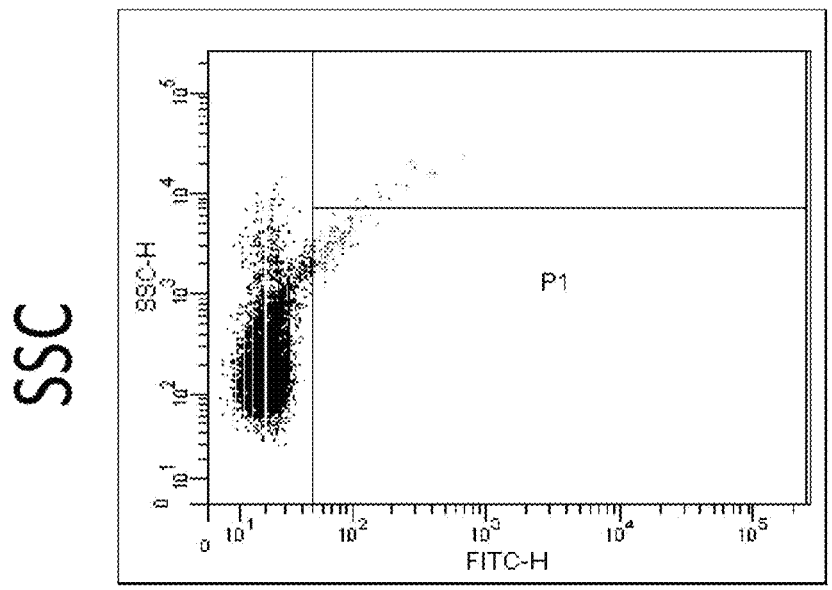
FIGS. 1*a*, 1*b*, 1*c*, 1*d* and 1*e* shows Flow cytometric analysis of *Bacillus coagulans* MTCC 5856 spores 10 mg of dry spores were suspended in 1 ml of phosphate buffered saline (PBS) and activated for 30 min at 75° C., followed by fluorescent staining as described in the Example Data represents mean±standard deviation of at least 3 independent experiments.
Figure 1B:
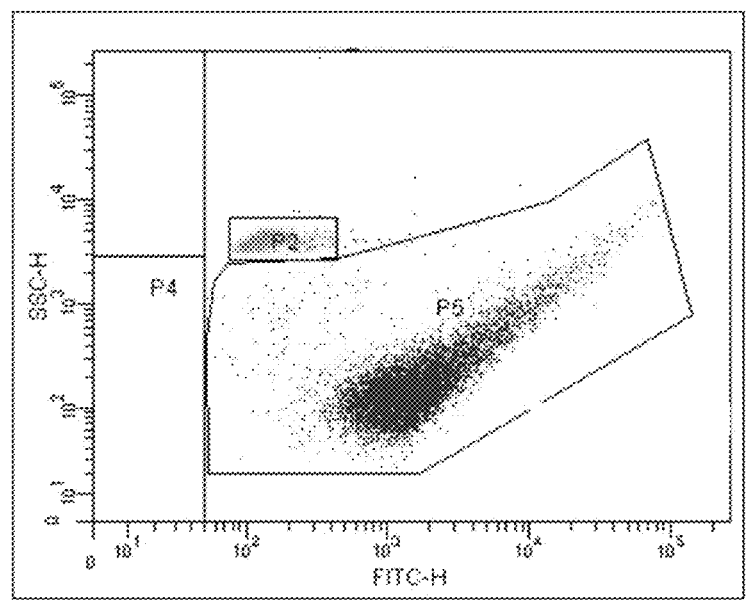
Figure 1C:
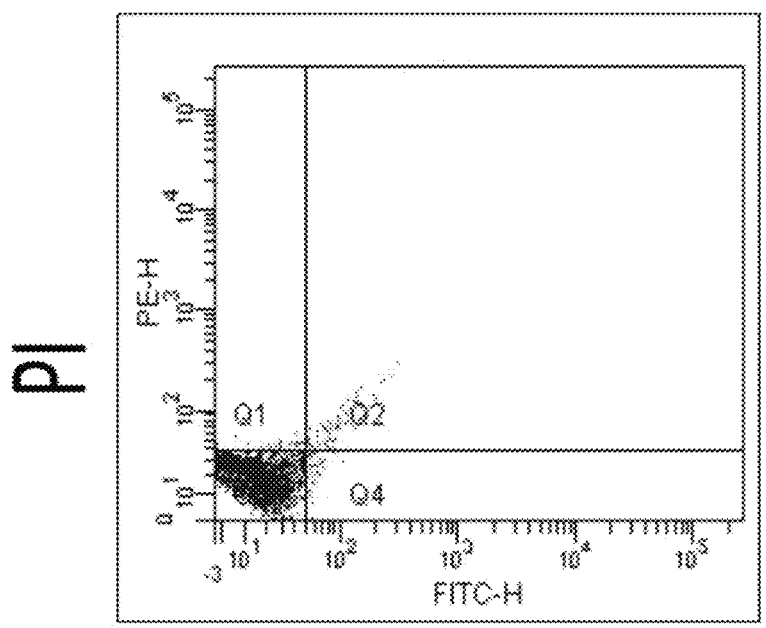
Figure 1D:
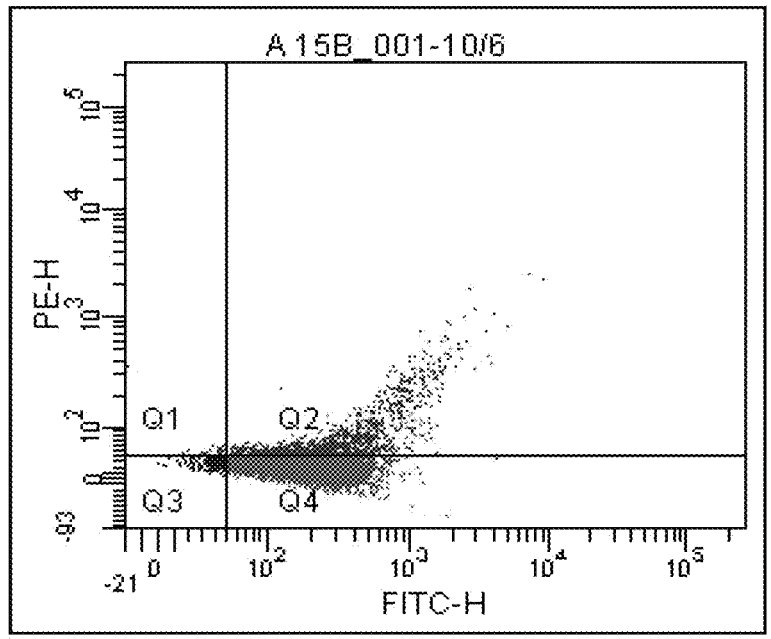
Figure 1E:
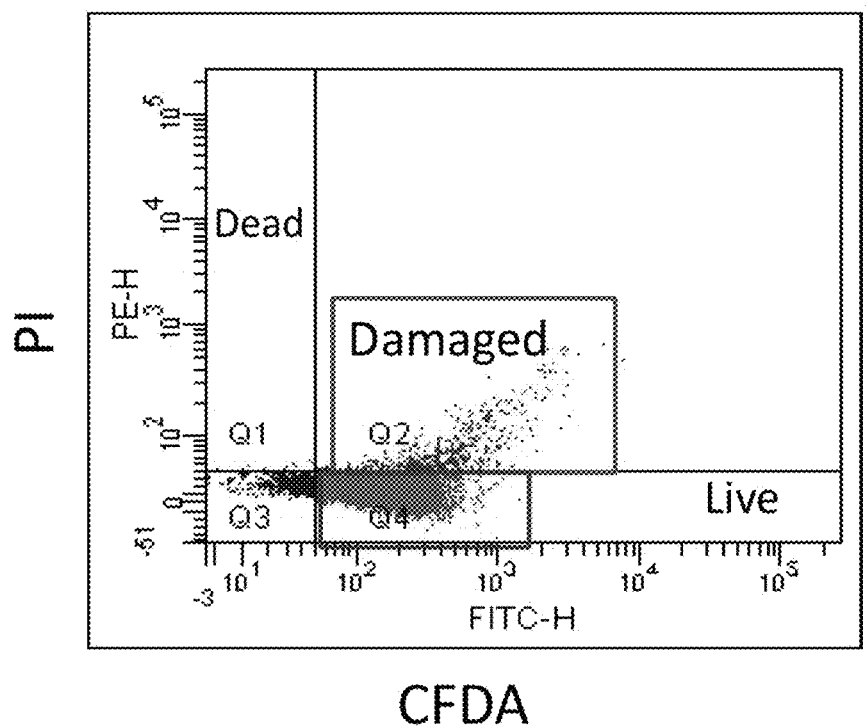
Figure 2A:
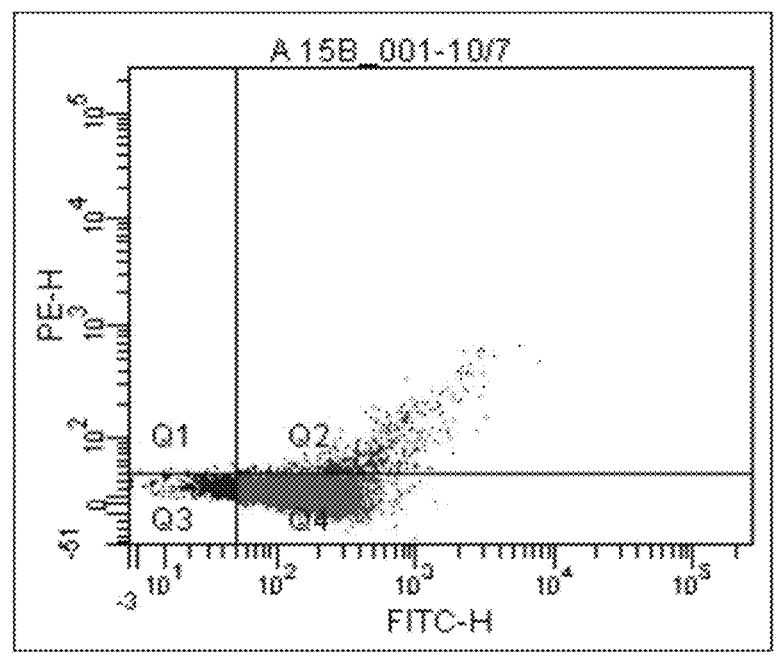
Figure 2B:
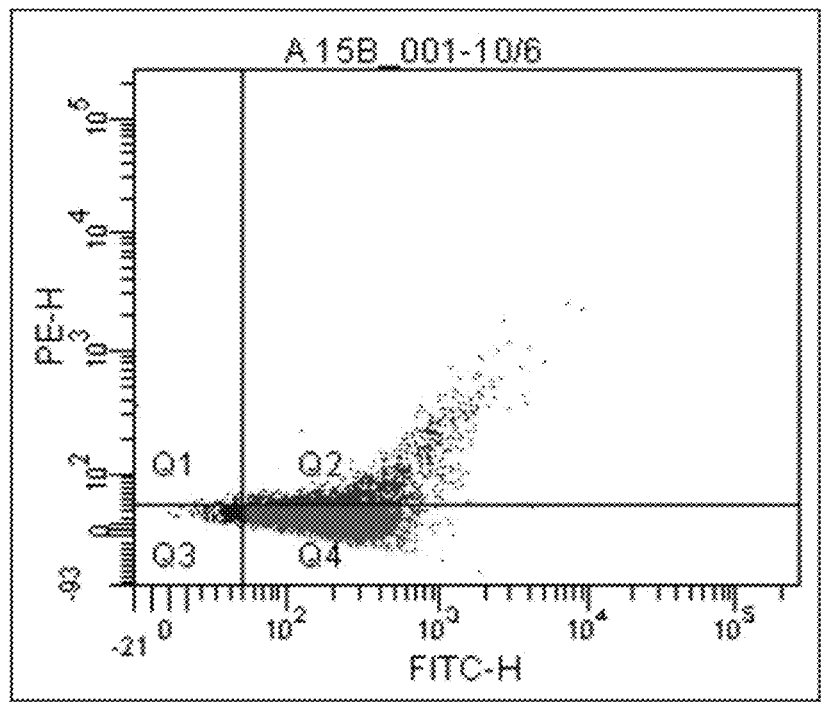
Figure 2C:
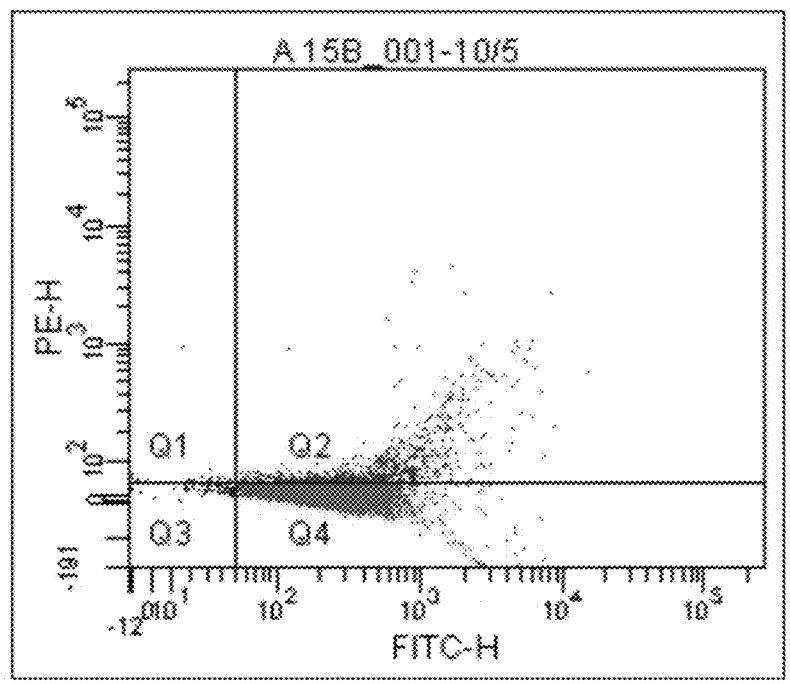
Figure 2D:
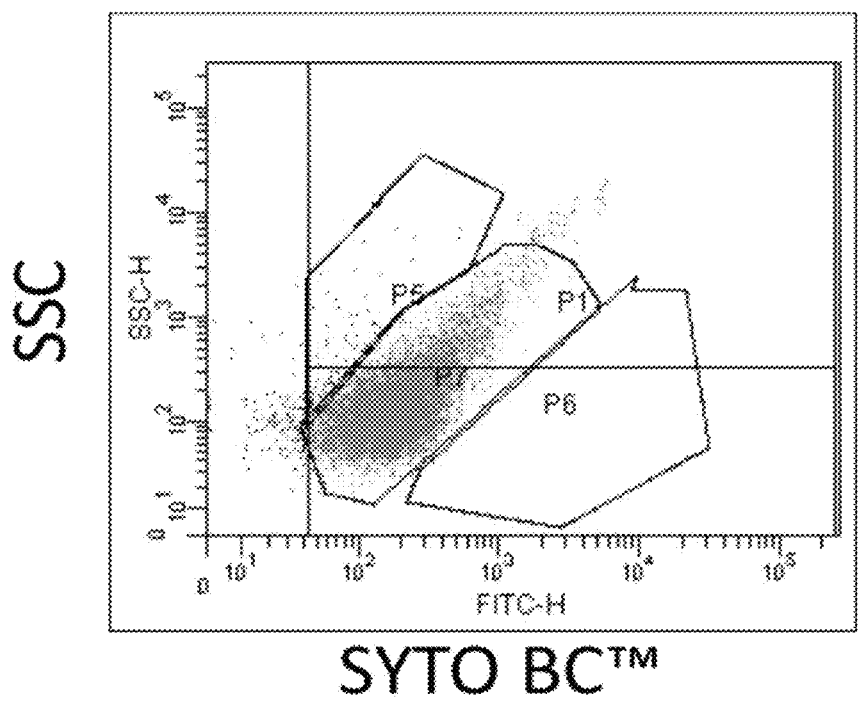
Figure 2E:
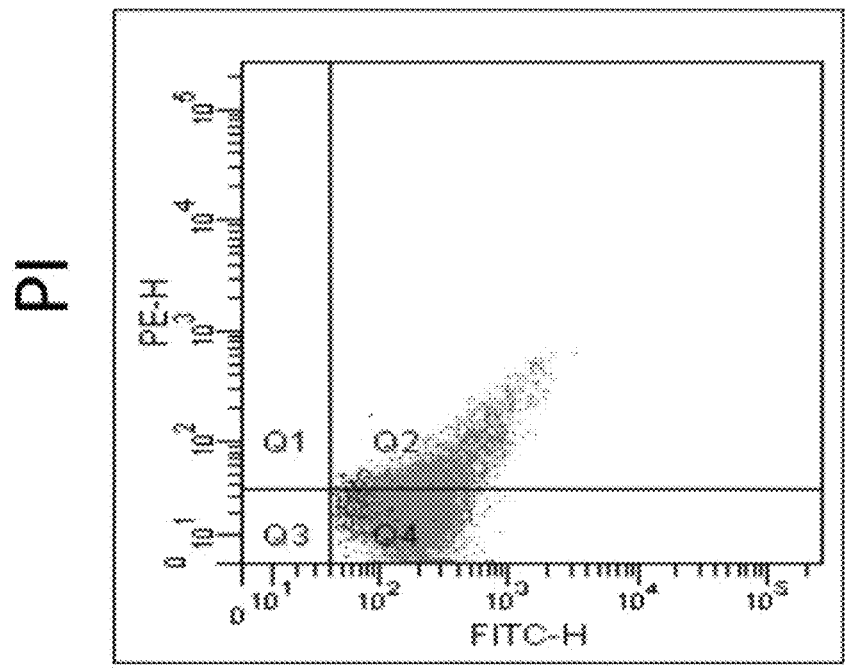
Figure 2F:
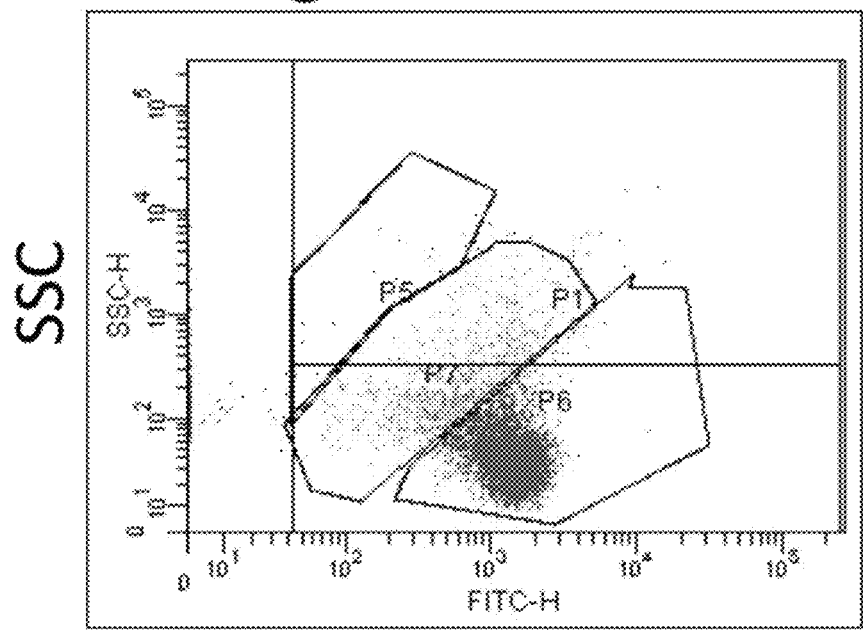
Figure 2G:
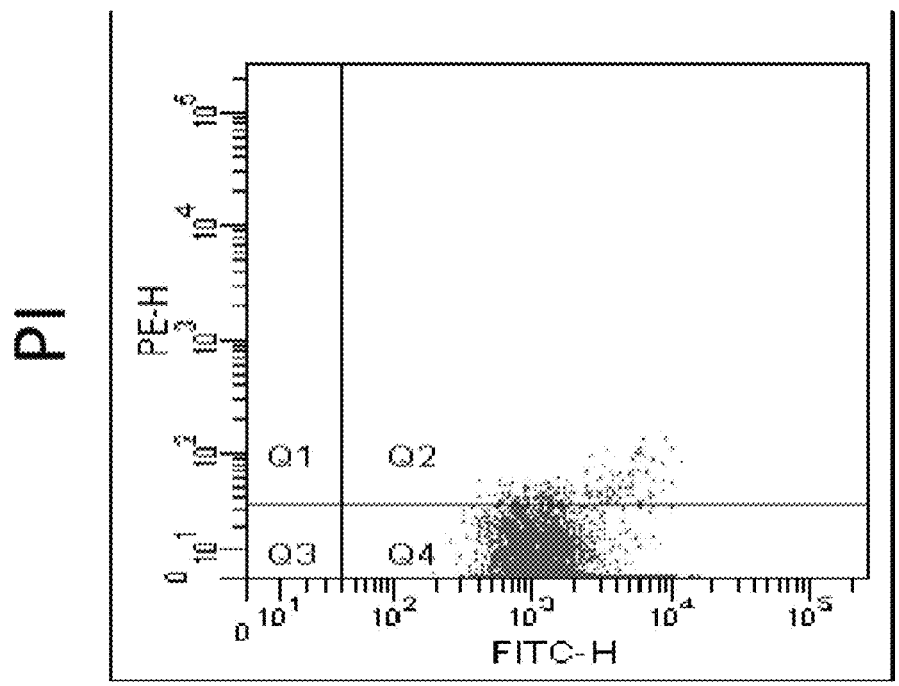
Figure 2H:
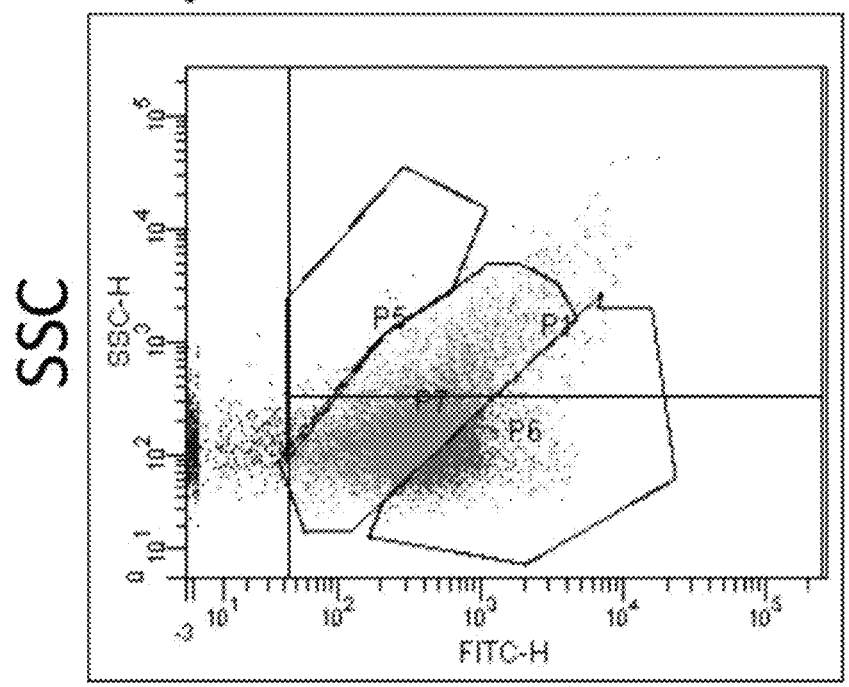
Figure 2I:
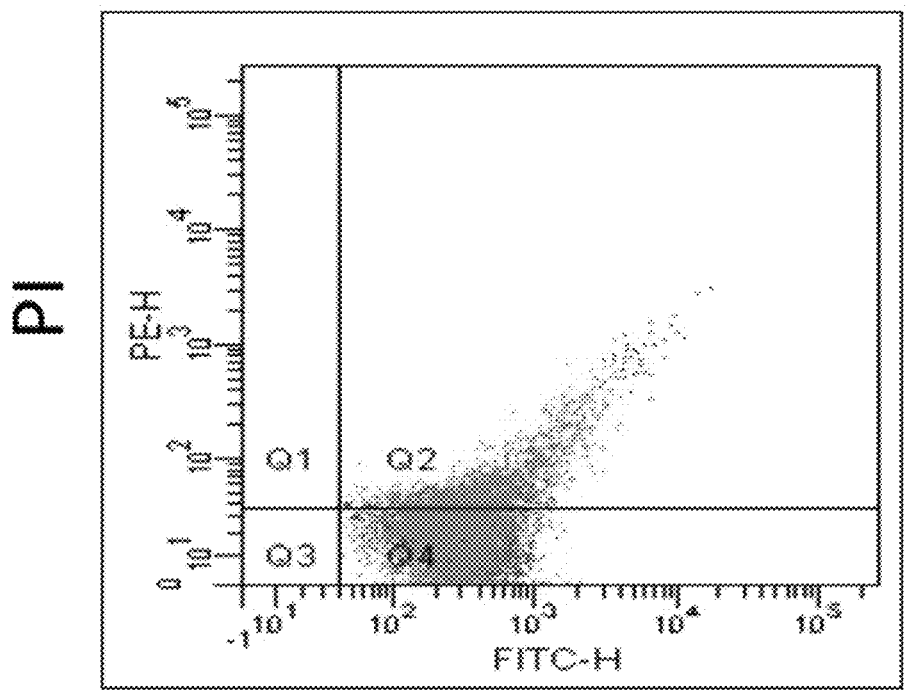
Figure 2J:
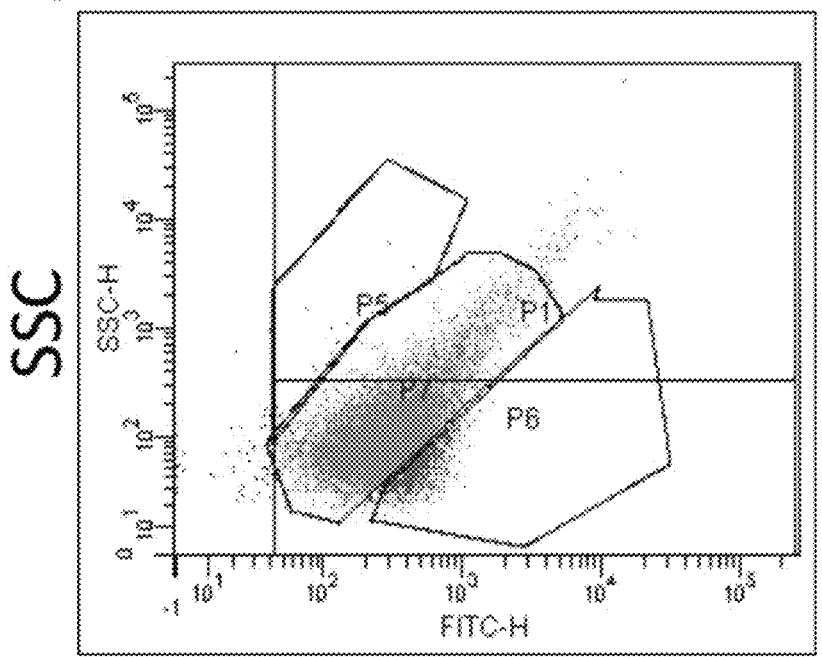
Figure 2K:
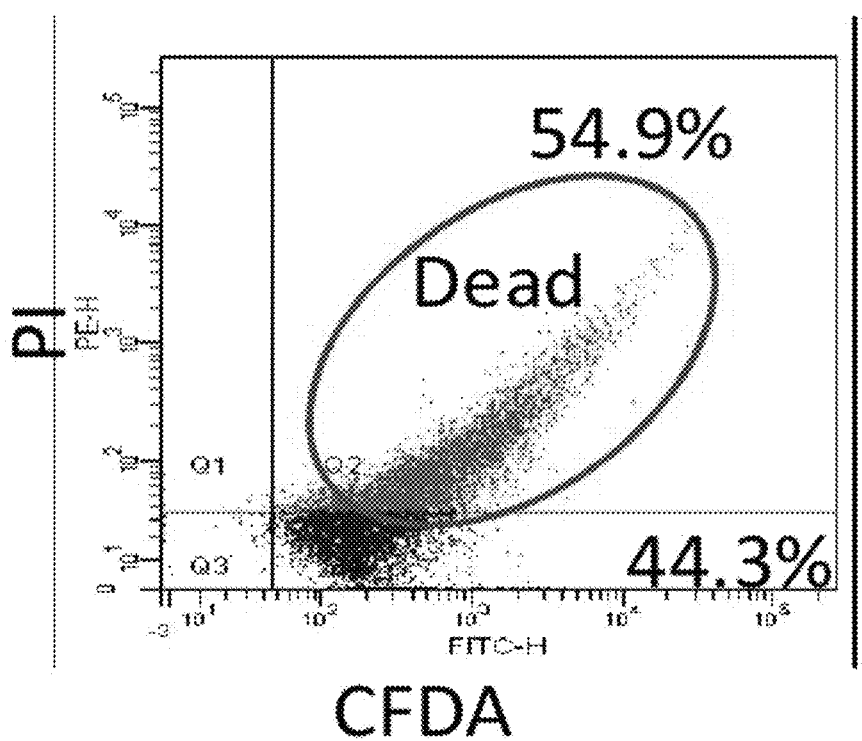
Figure 3A:
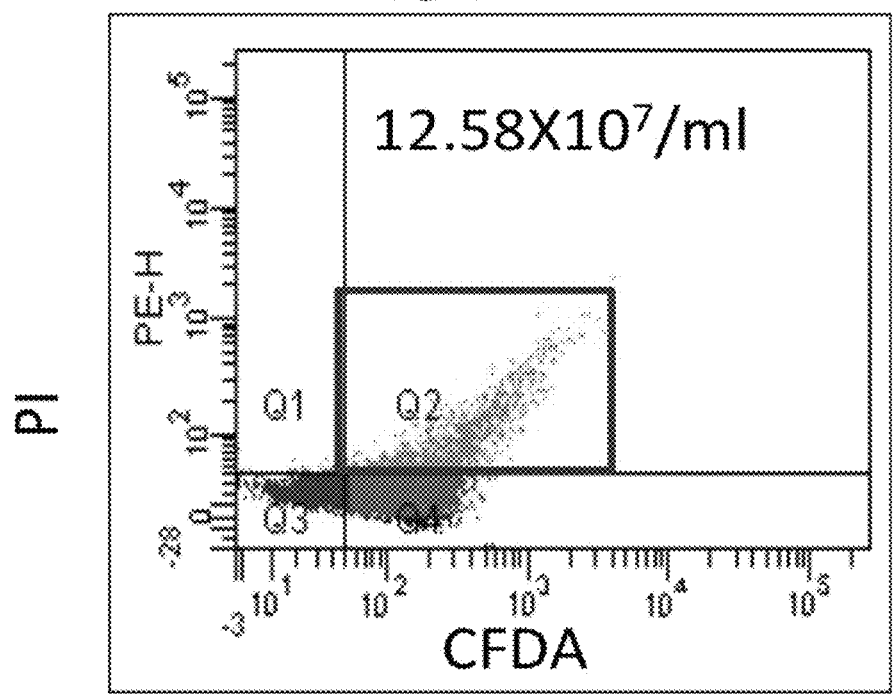
Figure 3B:
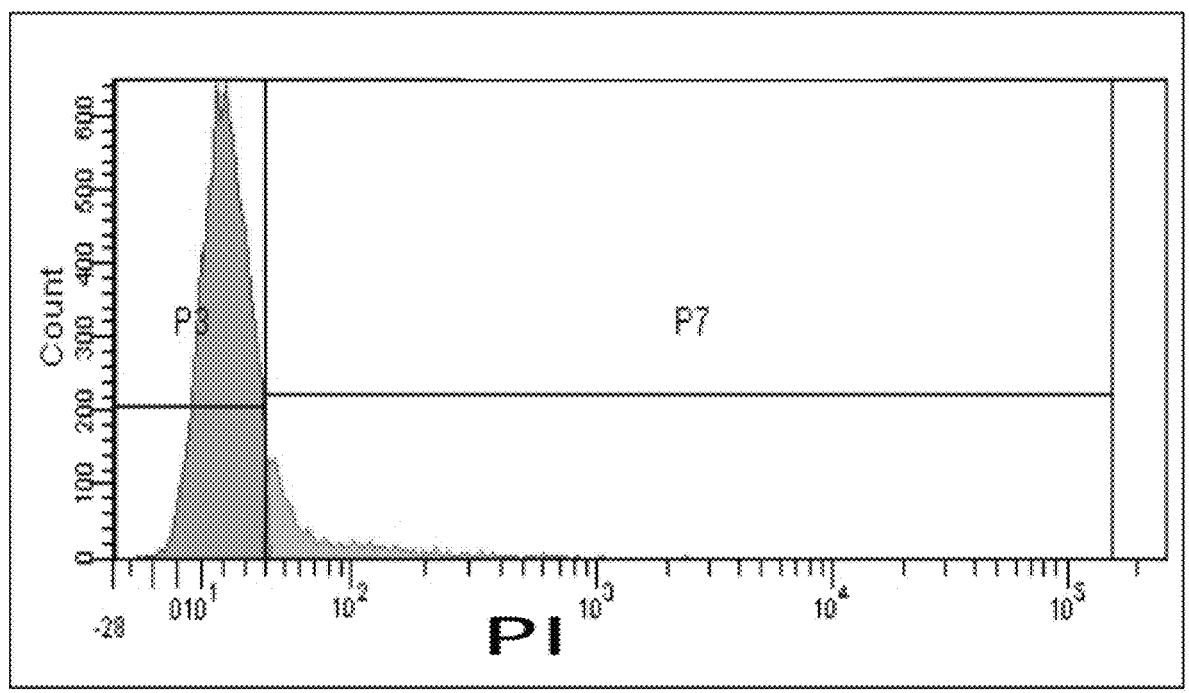
Figure 3C:
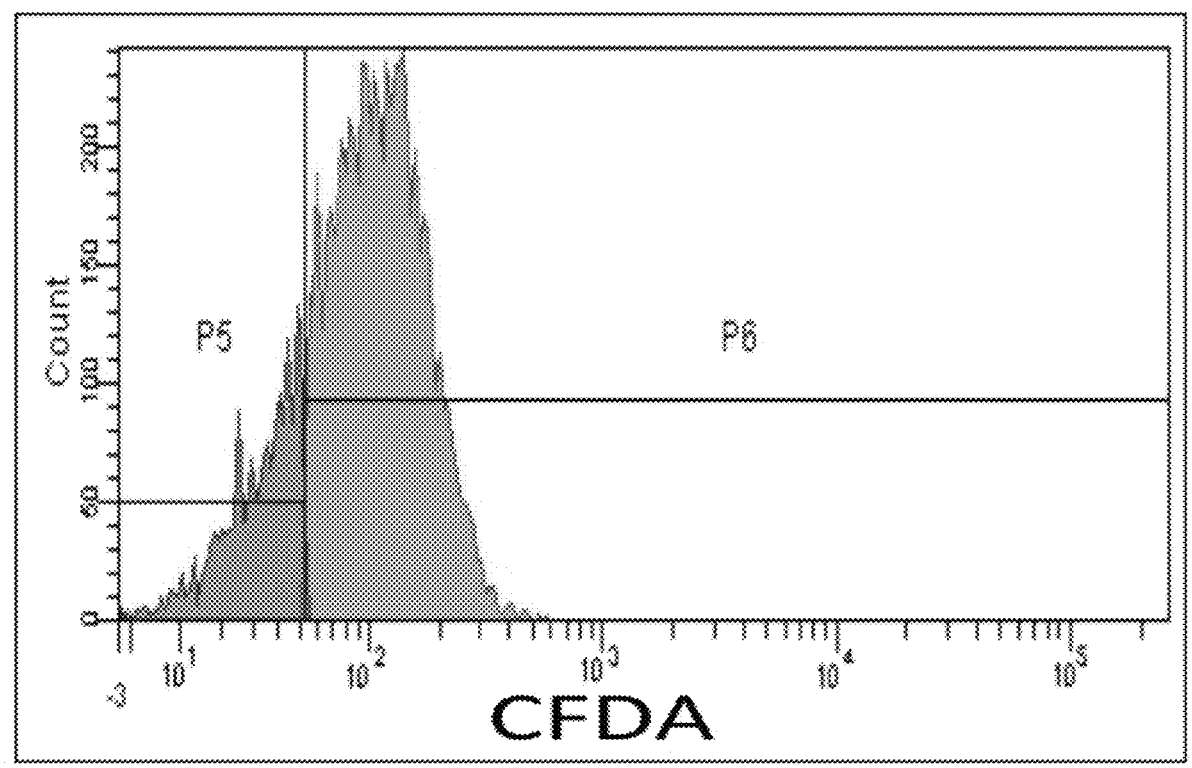
Figure 3D:
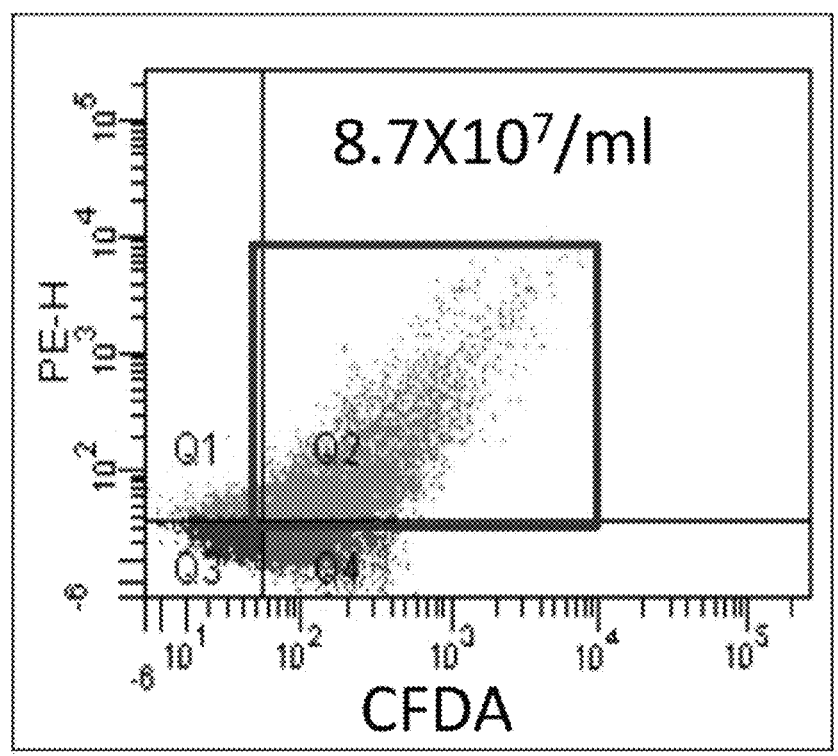
Figure 3E:
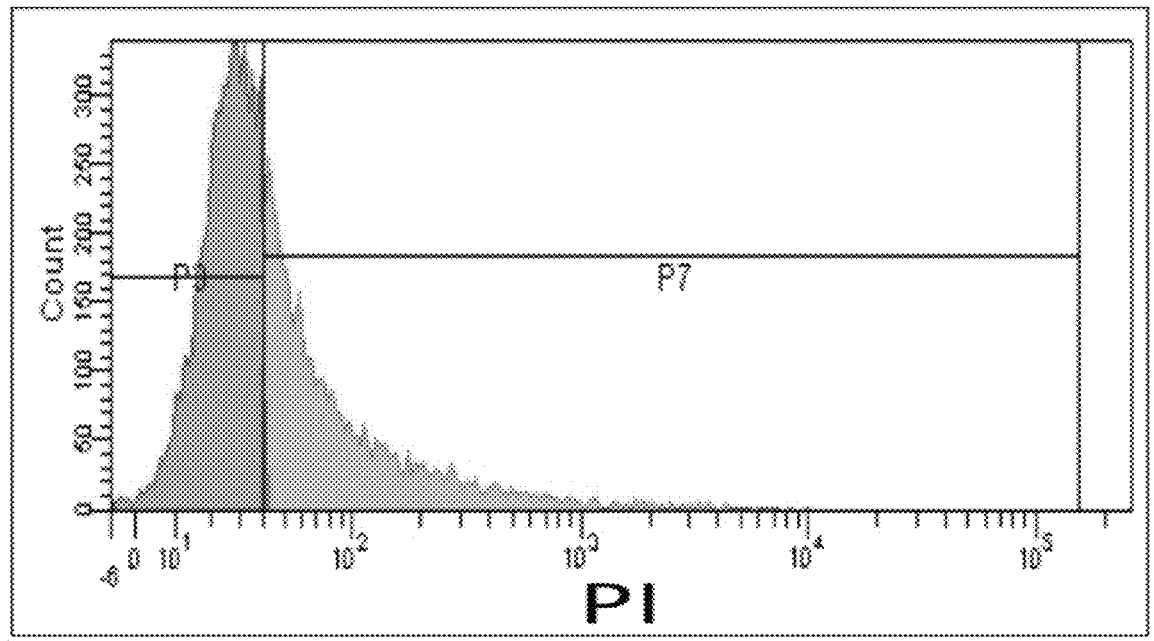
Figure 3F:
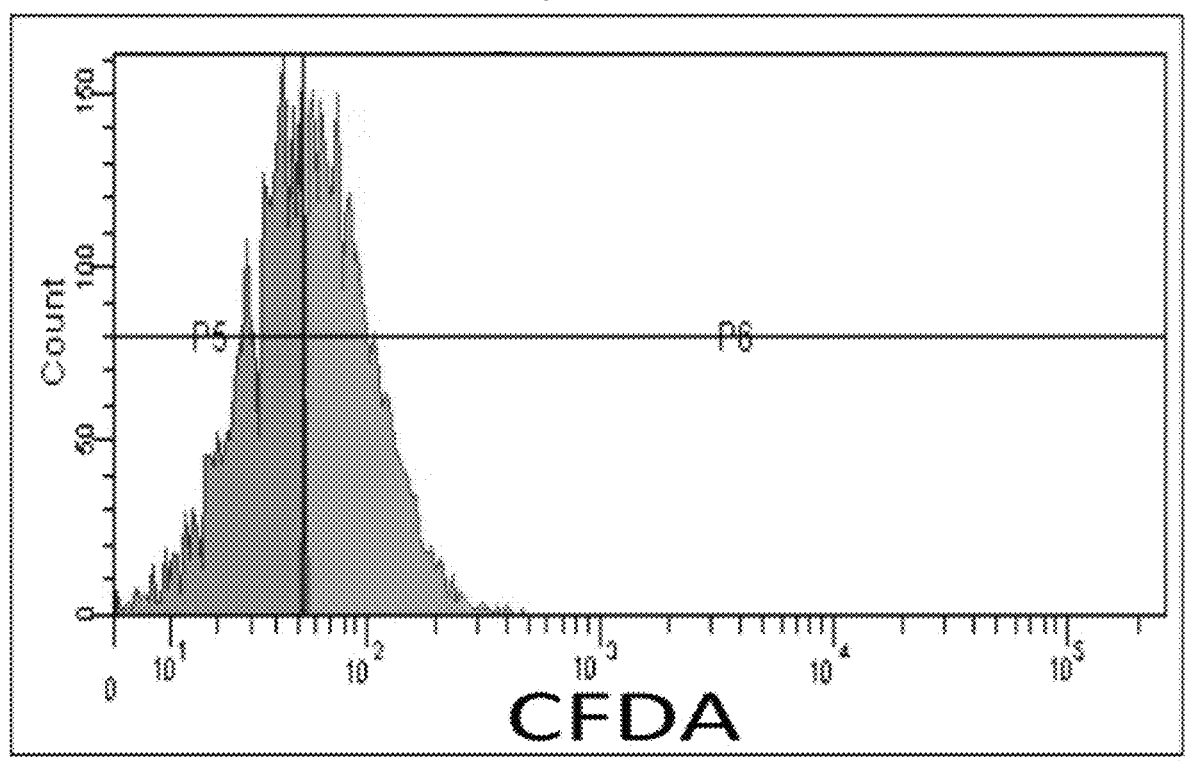
Figure 3G:
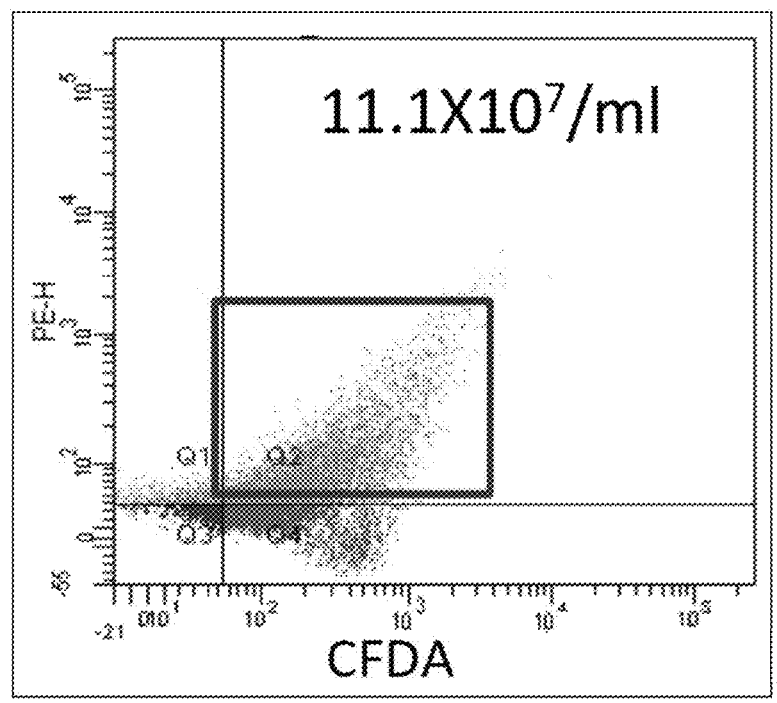
Figure 3H:
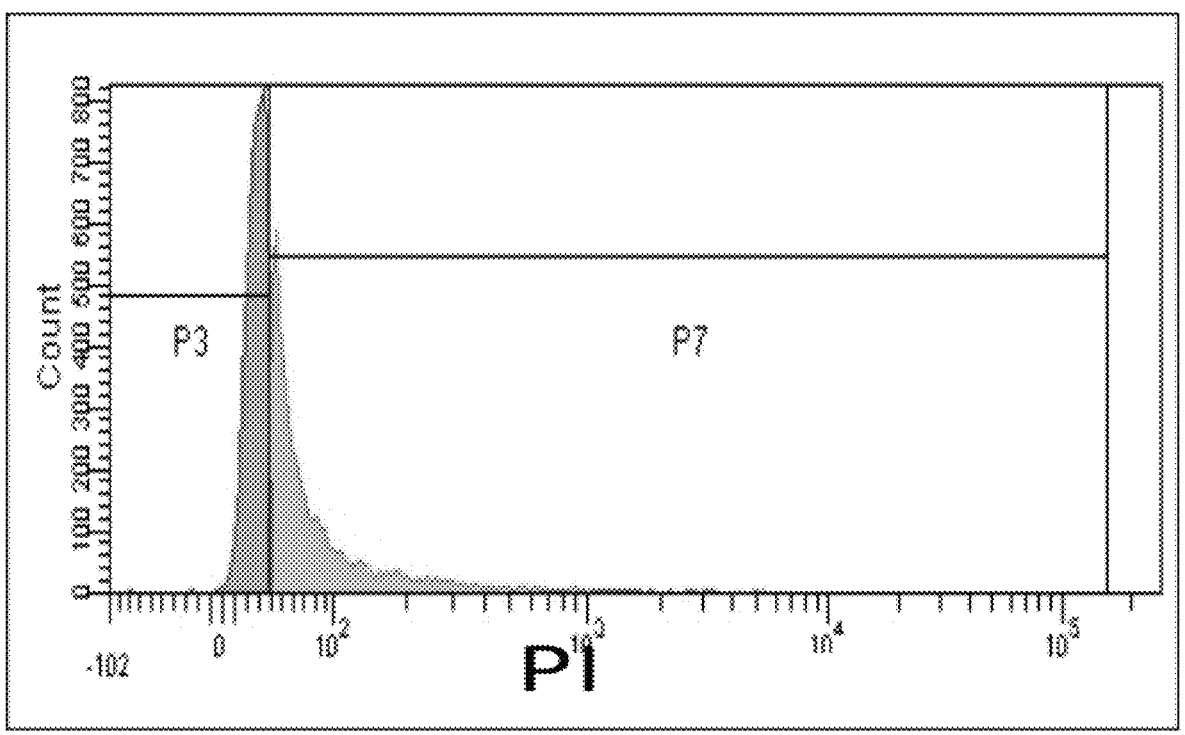
Figure 3I:
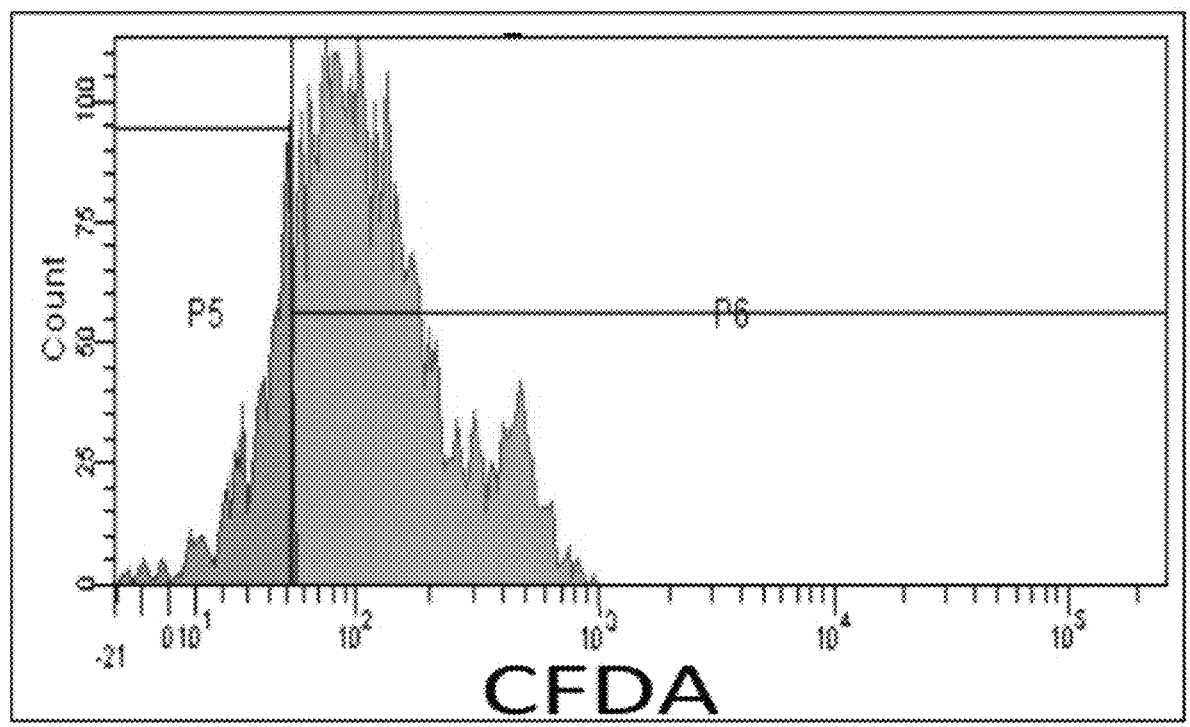
Figure 3J:
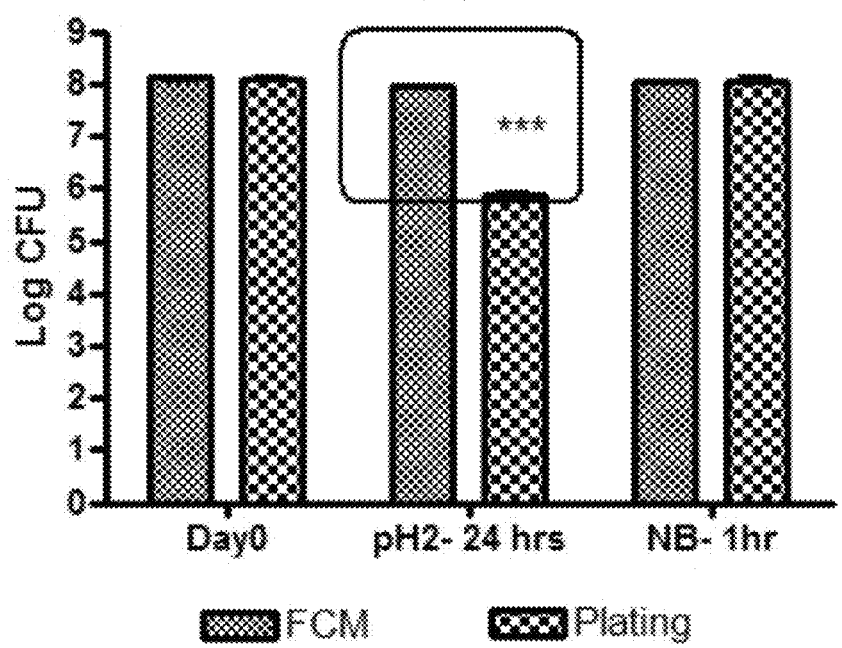

1*a* and 1*b*: Gating strategy for SYTOBC™ staining—The microbeads and the stained spores are gated separately based on unstained control 1*c* and 1*d*: Gating strategy for CarlDoxyfluorescein diacetate (cFDA) and Propidium iodide (PI) staining. The dot plot represents a double staining for both cFDA and PI. The quadrant 4(Q4) represents live cells, Q1—dead cells and Q2 damaged cells. The double positive cells were not considered for enumerating the live spores.

1*e*: Representative dot plot for the FCM analysis of Live and Dead spores

FIGS. 2*a*, 2*b*, 2*c*, 2*d*, 2*e*, 2*f*, 2*g*, 2*h*, 2*i*, 2*j* and 2*k* shows validation of Flow cytometry 2*a*, 2*b* and 2*c*: Spore suspension was diluted and each dilution was analysed by FCM as described earlier. Quantitative analysis is given in the Table 2.

2*d* and 2*e*: FCM analysis of spores

2*f* and 2*g*: vegetative cells and

2*h* and 2*i*: a mixture of spores and vegetative cells and

2*j* and 2*k*: killed cells

FIGS. 3*a*, 3*b*, 3*c*, 3*d*, 3*e*, 3*f*, 3*g*, 3*h*, 3*i* and 3*j* shows (Viable but non culturable bacteria) VBNC and Resuscitation count as measured by FCM The spore suspension (10 mg/ml) was incubated in 0.1M acetate buffer (pH 2) for 24 hours, followed by washing and suspension in Nutrient Broth (NB) and incubated at 37° C. for 60 minutes. The viable spores were enumerated by both FCM and plate count as described earlier. Data represents mean±standard deviation of at least 3 independent experiments.

FIGS. 4*a*, 4*b*, 4*c* and 4*d* shows spore viability in commercial preparations Viability of *Bacillus coagulans* spores in tablets, capsules and Orange juice: Total count and live spore count were determined by FCM. Data represents mean±standard deviation of 3 independent experiments.

FIGS. 5*a*, 5*b*, 5*c*, 5*d* and 5*e* shows comparative stability of probiotics by flow cytometry Bacterial count was assessed by flow cytometry (FCM) as described earlier. All the probiotic formulations were used before their expiry date. Probiotic E is a commercial preparation of *Bacillus coagulans* MTCC 5856. CFDA positive cells were taken as live cells. Data represents mean±standard deviation of 3 independent experiments.

A—*Bifidobacterium infantis*
B— *Lactobacillus rhamnosus* GG
C— *Lactobacillus' acidophilus*
D—*Lactobacillus casei*
E—*Bacillus coagulans* MTCC 5856

DETAILED DESCRIPTION OF THE MOST PREFERRED EMBODIMENT (FIG. 1a, 1b, 1c, 1d, 1e, FIG. 2a, 2b, 2c, 2d, 2e, 2f, 2g, 2h, 2i, 2j, 2k, FIG. 3a, 3b, 3c, 3d, 3e, 3f, 3g, 3h, 3i, 3j, FIG. 4a, 4b, 4c, 4d, FIGS. 5a, 5b, 5c, 5d and 5e)

In the most preferred embodiment, the present invention relates to a probiotic composition containing *Bacillus coagulans* MTCC 5856, exhibiting increased viability and stability over wide range of pH compared to other probiotic strains.

In a related embodiment, the pH is 2.0, 7.0 and 9.0. In another related embodiment, the probiotic is selected from the group consisting of *Lactobacillus casei, Bifidobacterium infantis, Lactobacillus rhamnosus* and *Lactobacillus acidophilus*.

In another embodiment, the invention, discloses a flow cytometric method of detecting spores, vegetative cells and the number of viable and dead cells of *Bacillus coagulans* MTCC 5856, said method comprising steps of:
 a) Suspending dry spores of *Bacillus coagulans* MTCC 5856 in phosphate buffered saline (pH 7.4) to obtain a suspension
 b) Incubating the suspension of step a) in a water bath for 30 minutes at 75° C. and cooling to 45° C. to obtain a suspension
 c) Eumerating the viable count of the suspension of step a) and b) on glucose yeast extract agar
 d) Eumerating the viable count of the suspension of step a) and b) using flow cytometric analysis comprising steps of
  i) Double staining spore suspensions ($10^7$/ml) of step a) and b) separately with 50 µM cFDA at 37° C. for 60 minutes and with 10 µM PI in the last 10 min
  ii) Staining spore suspensions ($10^7$/ml) of step a) and b) separately with SYTO BC™ (dilution 1:1000) and calibrated suspension of polystyrene microspheres (dilution 1:100) at 37° C. for 10 min in separate tubes
  iii) Performing flow cytometric detection using voltage parameters set at FSC-430 units, SSC-425 units, HTC-280 units and PE-269 units
  iv) Determining the density of the bacteria in the sample from the ratio of bacterial signals to microsphere signals in the cytogram
  v) Calculating the total number of spores as detected by SYTO BC™ staining by the formula Total No of spores =

$$\frac{\text{\# Events in } SYTO\ BC^{TM+} \text{ region}}{\text{\# Events in beads}} \times 10^6 \times \text{dilution factor } (DF)$$

vi) Calculating the number of viable spores by the formula

No of viable spores =

$$\frac{\text{\# Events in } cFDA^+ \text{ region}}{\text{\# Events in beads}} \times 10^6 \times \text{dilution factor } (DF)$$

Or

No of viable spores =

$$\frac{\text{Total spores} - \text{\# Events in } PI^+ \text{ region}}{\text{\# Events in beads}} \times 10^6 \times \text{dilution factor } (DF)$$

In a related embodiment, the method of testing the viability of *Bacillus coagulans* MTCC 5856 is performed in, but not limited to, probiotic tablets, capsules, dairy products, beverages, confectioneries, cosmeceutical creams, mucosal preparations, and food substances.

The specific examples included herein below illustrate the most preferred embodiments of the present invention.

EXAMPLES

Example 1: Methods

Test material: *Bacillus coagulans* MTCC 5856 samples were manufactured by Sami Labs Limited (Bangalore, India) following proprietary, in-house, good manufacturing practices. Pure *Bacillus Coagulans* MTCC 5856 spores were spray-dried and, standardised with food grade maltodextrin (Sanwa Starch Co. Ltd, Kashihara, Nara, Japan), to achieve the desired concentration of $15 \times 10^9$ CFU per gm of the finished product in powder form. The tablets and capsules were manufactured by Sabinsa Corporation, Payson, Utah. USA. Commercial preparations of other Probiotics were purchased from the market and used within their expiry date.

Sample Preparation for Flow Cytometry

For FCM analysis and viable count estimation, 10 mg of spores ($15 \times 10^9$/g) were suspended in 1 ml of sterile phosphate buffered saline (PBS, pH 7.4) and incubated in a water bath for 30 min at 75° C., followed by immediate cooling to below 45° C. This suspension was taken for either FCM analysis or further serially diluted in sterile PBS and the viable count was enumerated by plating on glucose yeast extract agar (HiMedia, Mumbai, India) as described earlier. One set of spores were analysed by FCM without the activation step at 75° C. for 30 minutes. Each experiment was repeated thrice in duplicates. Average mean of spore viable counts were expressed in logo CFU.

Fluorescent Staining

The fluorescent stains used were cFDA, PI, and SYTO BC™ and calibrated suspension of polystyrene microspheres (ThermoScientific Inc.). Double staining with cFDA and PI were carried out by incubating the spore suspension ($10^7$/ml) with 50 µM cFDA at 37° C. for 60 minutes in and 10 µM PI in the last 10 min. SYTO BC™ was diluted to 1000 times and the microbeads 100 times to get IX concentration of SYTO BC™ and $1 \times 10^6$ beads/ml. Spores were stained at 37° C. for 10 min in a separate tube.

Flow Cytometry

FCM acquisition was performed with a Canto II cytometer, and the data analysis with Diva software 6.2.1(BD biosciences, CA, USA). Cytometry set up and tracking (CST) beads (BD biosciences) were used to standardize the flow cytometer setup as per the manufacturer's instructions. All the buffers used for flow cytometry were filtered through 0.2 micron filter to prevent background bacterial noise. The filtered buffers were run as a negative control and threshold values were set at 2000. Forward and side scatter voltages for the photomultiplier tube (PMT) were adjusted by running the sterile buffer and buffer containing bacteria. Fluorescent voltages were adjusted based on stained and unstained samples. Compensation controls were run with each set of experiments to minimise the overlap of FITC (cFDA) & PE (PI) during double staining. The final PMT voltage parameters were set at FSC-430 units, SSC-425 units, FITC-280 units and PE-269 units. Auto florescence gating was carried out using unstained spores. Calibrated suspension of polystyrene microspheres can be distinguished from SYTO BC™ on a plot of forward scatter versus fluorescence. The density of the bacteria in the sample can be determined from the ratio of bacterial signals to microsphere signals in the cytogram.

Calculations

Total number of spores as detected by SYTO BC™ staining was calculated by $$\text{Total No of spores'} = \frac{\text{\# Events in } SYTO\ BC^{TM+} \text{ region}}{\text{\# Events in beads}} \times 10^6 \times \text{dilution factor } (DF)$$

The numbers of viable spores were calculated by $$\text{No of viable spores'} = \frac{\text{\# Events in } CFDA^+ \text{ region}}{\text{\# Events in beads}} \times 10^6 \times \text{dilution factor } (DF)$$

Or $$\text{No of viable spores} = \frac{\text{Total spores} - \text{\# Events in } PI^+ \text{ region}}{\text{\# Events in beads}} \times 10^6 \times \text{dilution factor } (DF)$$

Validation of Flow Cytometry

A spore stock of $15 \times 10^7$ spores/ml was prepared from *Bacillus coagulans* MTCC 5856 (strength of $15 \times 10^9$/g). The spore suspension was serially diluted in PBS and the count was enumerated from each dilution individually by FCM and compared with plate count. To understand the differentiation between spores and vegetative cells, spores were grown in nutrient broth (Hi Media, India) overnight and the cells were either analysed individually or after mixing with fresh spores. Alternately, the vegetative cells were exposed to isopropyl alcohol and then mixed with spores to show the sensitivity of FCM in counting live and dead cells.

VBNC and Resuscitation

To study the proportion of VBNC spores and their resuscitation under favourable environment for germination, the spore suspension ($1.5 \times 10^7$/ml) was incubated in 0.1M acetate buffer (pH 2) for 24 hours. The spores were centrifuged, washed with PBS twice and suspended in nutrient broth and incubated at 37° C. for 60 minutes. The viable spores were enumerated by both FCM and plate count.

Spore Count in Commercial Preparations

The entire content of the capsule was suspended in 50 ml PBS while the tablet was weighed and crushed and thoroughly and suspended in 50 ml of PBS. The samples were analysed by FCM as well as plate count as described earlier.

Spore Count in Orange Juice

Predetermined number spores with overages were mixed in commercial orange juice purchased from the market. The juice was stored at 4° C. for 24 hours and the number of spores were determined by both FCM and plate count method.

Commercial Probiotics

Four probiotics were taken for comparison with *Bacillus coagulans* MTCC 5856. They were purchased from local supermarkets or obtained from the manufacturers or distributors. All were stored according to label and all were used for study before their expiry dates. The tablets and capsules were processed for flow cytometry without the activation step as described earlier Statistical Analysis Graph Pad prism software version 5.01 (GraphPad Software, Inc., La Jolla, Calif., USA). Results were expressed as Mean±Standard deviation Mann-Whitney test was used for analysis of significance and a P value of <0.05 was considered statistically significant Example 2: Results Enumeration of *Bacillus coagulans* Spores by Flow Cytometry The spores were distributed in four quadrants of the dot plot following Flow cytometry. The quadrant 1(Q1) represented the PI stained dead cells, Q2 had spores which were stained by both PI and CFDA, which were categorised as damaged cells. Live spores could be seen as CFDA positive cells in Q3, while few spores were seen in Q4 which were unstained spores. We considered the CFDA$^+$PI$^-$(Q3) cells as live spores for the enumeration of spore counts. Total count of spores as determined by SYTO BC™ staining was found to be 15.72±0.92 billion/g. The viable spores as calculated by (CFDA+) cells was found to be 14.07±0.62 billion/gram, and that by subtracting the PI positive (dead) cells from total count was 13.97±0.42 billion/g (FIGS. 1a, 1b, 1e, 1d and 1e), which were highly comparable. The total numbers as well as live count were slightly higher when the activation step was omitted before FCM analysis (16.6=1:0.23) (FIG. 1a, 1b, 1e, 1d, 1e and Table 1).

Table 1: Table showing, the calculation of viable spores

TABLE 1

| Parameter | Count x $10^9$/g |
| --- | --- |
| SYTO ™ BC$^+$ Total Spores | 15.94 ± 0.92 |
| CFDA$^+$ (Live) | 14.07 ± 0.61 |
| PI$^+$ (dead/damaged) | 1.74 ± 0.50 |
| Live Spores Total-PI$^+$ | 13.97 ± 0.42 |
| Total spores without activation | 18.83 ± 0.08 |
| Live spores without activation | 16.60 ± 0.23 |

Validation of Flow cytometry

To validate the method of spore enumeration by FCM, we diluted the spore stock and counted the total number and viable spores by FCM in each dilution. As shown in (FIGS. 2a, 2b, 2c, 2d, 2e, 2f, 2g, 2h, 2i, 2j and 2k), FCM was sensitive to count the spores from a stock of $10^7$ to $10^5$ per ml. Tenfold dilution of spores was reflected in the FCM count resulting in comparable total and viable count per gram of spores irrespective of the dilution used for enumeration. Dilution below $10^4$ spores per ml, were not taken as it was not feasible to collect 10000 events for the FCM analysis. The viable spore count of freshly prepared suspension of spores by FCM (14.02±0.78 billion/g) was highly comparable to the plate count (13.24±2.9 billion/g, further validating the method for the enumeration of *Bacillus coagulans* MTCC 5856. To understand the difference between spores and vegetative cells, we allowed the spores to germinate and grow in nutrient broth overnight, and analysed the cells by FCM. The vegetative cells were seen as a distinct population in comparison to spores in the SYTO BC™ stained plots. The live and dead staining by CFDA and PI could not differentiate the spores from vegetative cells. To establish the sensitivity of the assay, we used killed vegetative cells mixed with spores for FCM analysis in equal proportion (FIGS. 2a, 2h, 2c, 2d, 2e, 2f, 2g, 2h, 2i, 2j and 2k). Mixing spores and killed cells showed an increase in dead cells as stained by PI (54.9%) while live spores were 44.3%. These results establish the robustness of FCM as an accurate technique to identify spores, vegetative cells and the number of viable and dead cells in the given population (FIG. 2a, 2b, 2c, 2d, 2e, 2f, 2g, 2h, 2i, 2j, 2k and Table 2).

TABLE 2

| Spore Strength | Spore count/ml | |
|---|---|---|
| | Total count SYTO ™ BC | Viable count CFDA |
| $10^7$/ml | $15.01 \pm 0.51 \times 10^7$ | $14.02 \pm 0.49 \times 10^7$ |
| $10^6$/ml | $15.71 \pm 0.92 \times 10^6$ | $14.07 \pm 0.61 \times 10^6$ |
| $10^5$/ml | $15.09 \pm 0.05 \times 10^5$ | $13.71 \pm 0.12 \times 10^5$ |
| | Viable Spore count | |
| Plating | 13.24 ± 2.9 billion/gram | |
| FCM | 14.02 ± 0.78 billion/gram | |

VBNC and Resuscitation

VBNC is a state which is induced by unfavourable environmental conditions. We used acidic pH to induce VBNC in *Bacillus coagulans* MTCC 5856. The live count of spores before incubation in acidic buffer was $13.12\pm0.76\times10^7$/ml by FCM and $12.5\pm0.84\times10^7$/ml by plating. After 24 hours of incubation at room temperature in acetate buffer at pH 2.0, the spore count estimated by plating reduced to $7.25\pm1.06\times10^5$/ml, while it was $8.7\pm0.19\times10^7$/ml by FCM. Interestingly the numbers of spores in the double positive quadrant were higher after 24 hours exposure to stressful condition, suggesting cell damage. Incubation in nutrient broth for 60 minutes restored the spore viability as seen by an increase in plate count to $11.5\pm2.1\times10^7$/ml and $11.13\pm0.31\times10^7$/ml by FCM (3a, 3b, 3c, 3d, 3e, 3f, 3g, 3h, 3i and 3j).

Spore Count in Commercial Preparations

We then enumerated the viability of spores in capsules and tablet formulation since the process involved in the manufacture is known to affect the viability of probiotics. The numbers of viable spores were observed to be 2 billion in both capsule and tablet which was in accordance with the label on the capsules. The total count by FCM was found to be 3.54±0.68 billion/capsule while it was 4.6±0.63 billion/g in the tablet. The viable spores in the tablet as enumerated by FCM were $3.4\pm0.62\times10^9$ while in the capsule it was $2.25\pm0.26\times10^9$. The numbers of viable spores were not less than 2 billion as per the label in the commercial product by both FCM analysis and plate count (FIG. 4a, 4b, 4c, 4d, Table 3 and Table 4).

TABLE 3

| Count × $10^9$ | Total Spores | Viable Spores |
|---|---|---|
| FCM | 3.54 ± 0.68 | 2.25 ± 1.26 |

TABLE 4

| Count × $10^9$ | Total Spores | Viable Spores |
|---|---|---|
| FCM | 4.6 ± 0.63 | 3.4 ± 0.62 |

Spore Viability in Orange Juice

Figure 4A:
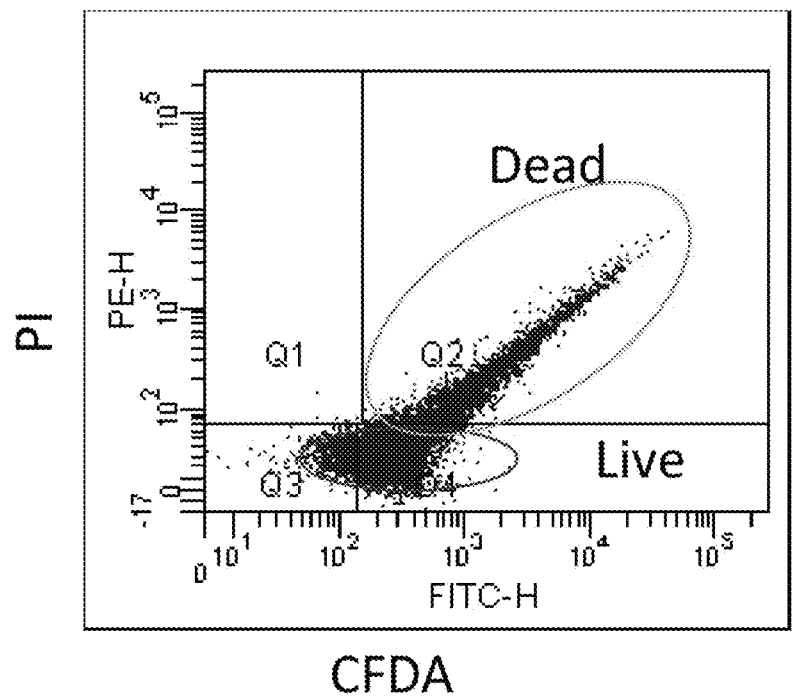
Figure 4B:
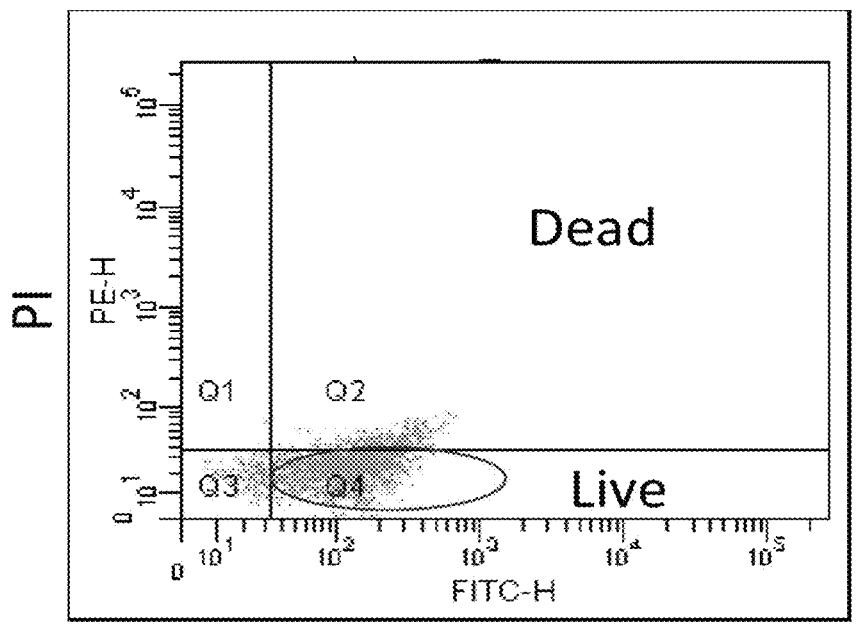
Figure 4C:
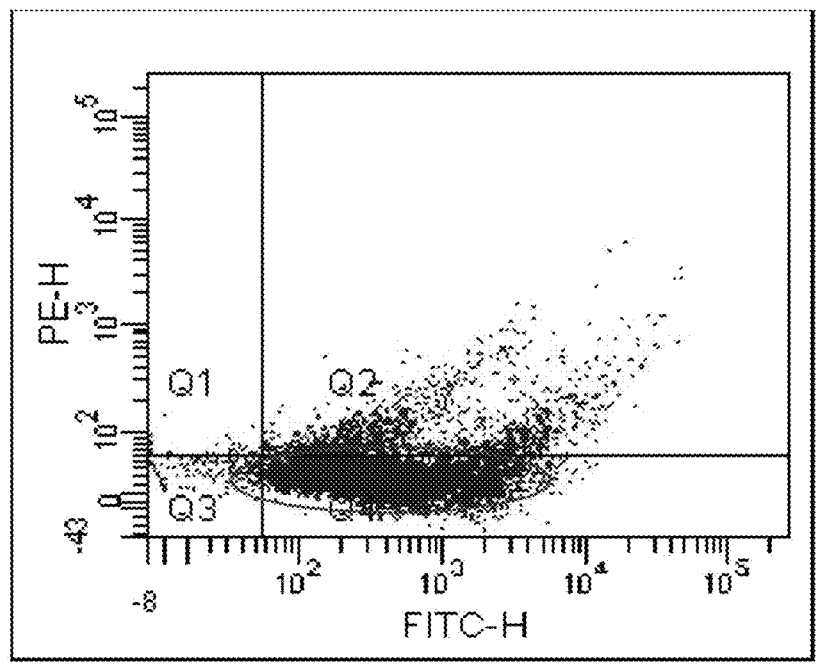
Figure 4D:
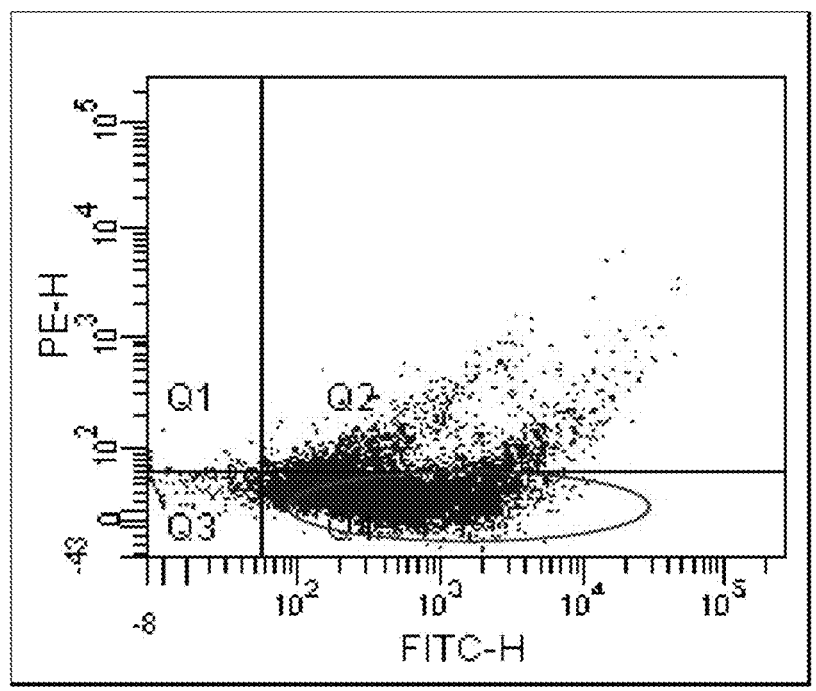
Figure 5A:
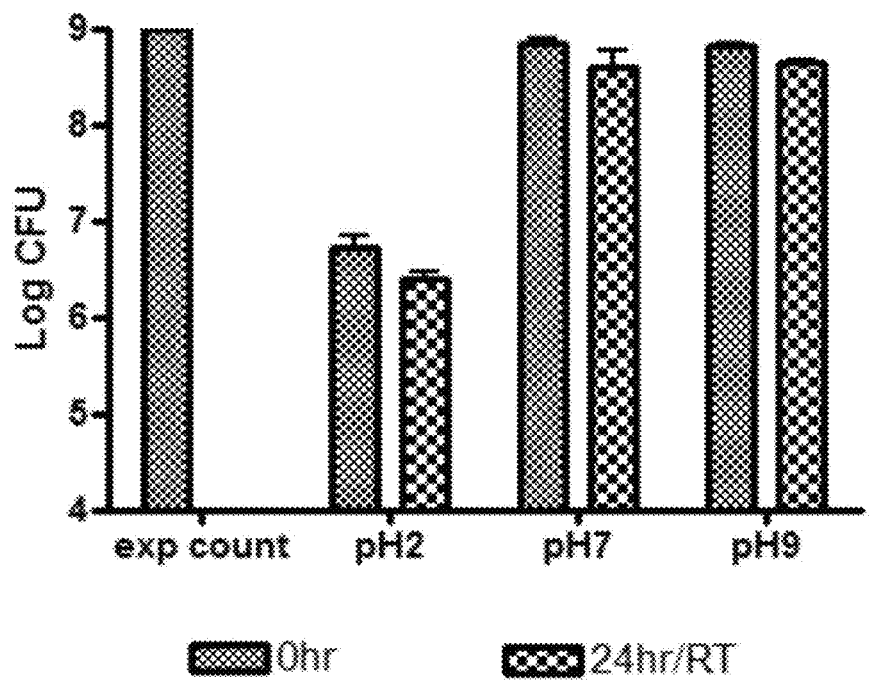
Figure 5B:
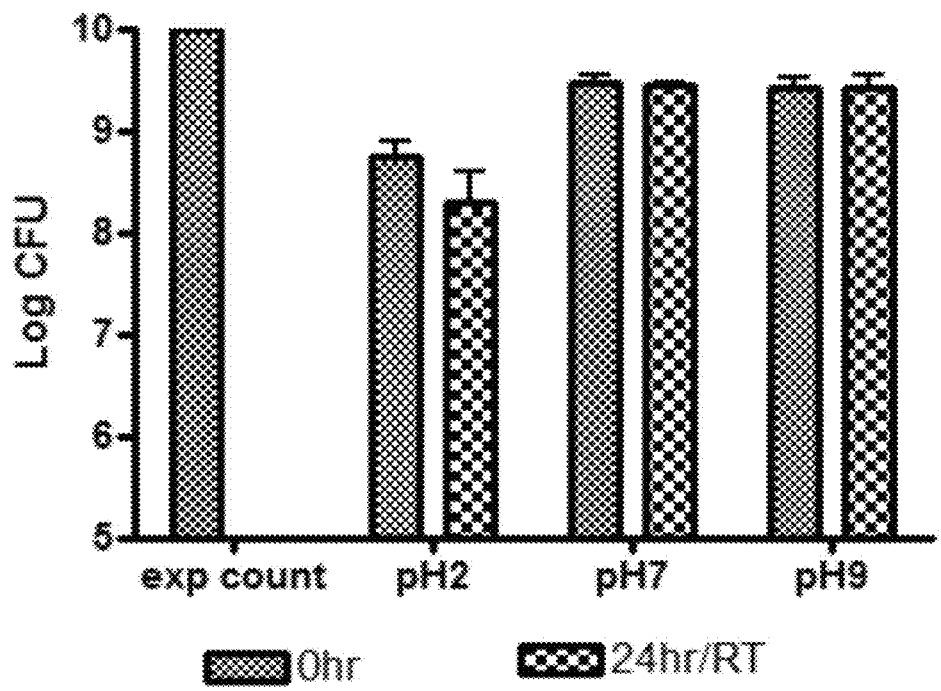
Figure 5C:
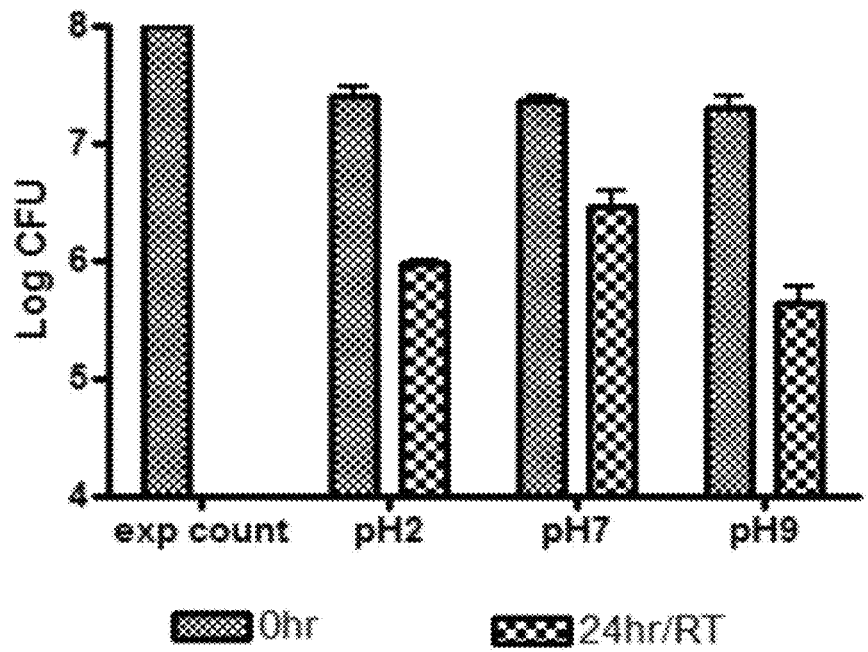
Figure 5D:
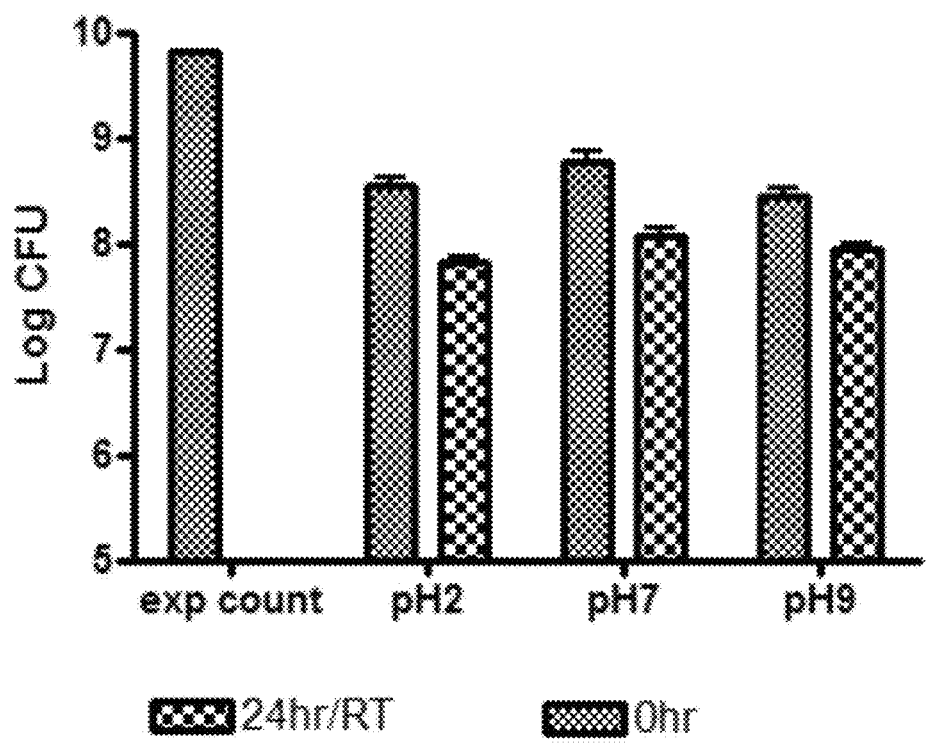

We next studied its viability in orange juice, which is a direct application of the probiotic in the market. Spores were added to commercial orange juice and the viability estimated by both FCM and plate count method after 24 hours. As shown in FIGS. 4c and 4d, FCM method was adaptable for the enumeration of spores from commercial preparation such as orange juice with considerable accuracy (Table 5).

TABLE 5

| Sample | Spores Mixed in Juice | Viable Spores |
|---|---|---|
| A | $2.5 \times 10^9$ | $1.8 \times 10^9$ |
| B | $3.0 \times 10^9$ | $2.2 \times 10^9$ |

Comparative Stability of Probiotics

Stability is an important criterion for Probiotics. Therefore we compared the viable count of commercial probiotic formulations with *Bacillus coagulans* MTCC 5856 at different conditions. *Bacillus coagulans* MTCC 5856 (Probiotic EB showed viability at neutral and alkaline pH and less than one log reduction in CFU at acidic condition even after 24 hours of incubation at room temperature. Probiotic A was stable at neutral and alkaline pH, but a reduction of 2.5 to 3 log in CFU was observed at acidic conditions. The CFU of Probiotic B was a log lower than expected value. By 24 hours 2 log reduction in CFU was observed at RT. Probiotic C was found, to be stable at neutral pH, while 1 and 2 log reduction in CFU was observed at alkaline and acidic pH. Under acidic conditions, Probiotic D showed good stability but 2-3 log reduction in CFU was observed after 24 hours incubation at RT (FIGS. 5a, 5b, 5e, 5d and 5e). Commercial Probiotics C and D were found to rapidly lose viability at room temperature but showed better stability when stored at 4° C. In comparison *Bacillus coagulans* MTCC 5856 (Probiotic E) spores from a commercial formulation was found to have good stability at room temperature (25° C.±4° C.) at acidic neutral as well as alkaline conditions as observed by Flow cytometry.

Example 3

Stability of *Bacillus coagulans* MTCC 5856

Stability of *Bacillus coagulans* MTCC 5856 at room temperature was tested for 0 hours to 2 months. The live cells were determined using flow cytometric analysis. The results are tabulated in Table 6.

TABLE 6

| Time | Live Count ± SD × $10^9$ in Neutral pH (7) | Live Count ± SD × $10^9$ in Alkaline pH (9) | Live Count ± SD × $10^9$ in Acidic pH (2) |
| --- | --- | --- | --- |
| 0 hours | 11.27 ± 2.92 | 11.97 ± 0.82 | 11.58 ± 0.82 |
| 24 hours | 7.1 ± 2.2 | 10.73 ± 1.92 | 8.7 ± 2.62 |
| 7 days | 6.92 ± 4.2 | 10.2 ± 0.99 | 3.01 ± 1.03 |
| 1 Month | 4.17 ± 0.35 | 10.22 ± 0.42 | 2.58 ± 0.08 |
| 2 Months | 3.76 ± 0.37 | 9.6 ± 0.52 | 2.18 ± 0.99 |

The results indicated that *Bacillus coagulans* MTCC 5856 is stable over a period of 2 months room temperature (25 to 30° C.).

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A flow cytometric method of detecting spores, vegetative cells and the number of viable and dead cells of *Bacillus coagulans* MTCC 5856, said method comprising steps of:
   a) Suspending dry spores of *Bacillus coagulans* MTCC 5856 in phosphate buffered saline (pH 7.4) to obtain a first suspension
   b) Incubating the suspension of step, a) in a water bath for 30 minutes at 75° C. and cooling to 45° C. to obtain a second suspension
   c) Enumerating the viable count of the first suspension and second suspension on glucose yeast extract agar
   d) Enumerating the viable count of the first suspension and second suspension using flow cytometric analysis comprising steps of:
      i) Obtaining as first aliquot of the first suspension containing $10^7$ spores/ml; obtaining a first aliquot of the second suspension containing $10^7$ spores/ml and staining each first aliquot separately with 50 μM carboxyfluorescein, diacetate (cFDA) at 37° C. for 60 minutes with adding 10 μM Propidinin Iodide (PI) to each cFDA stained first aliquot for the last 10 min of cFDA staining;
      ii) Obtaining a second aliquot of the first suspension containing $10^7$ spores/ml; obtaining a second aliquot of the second suspension containing $10^7$ spores/ml and staining each second aliquot with fluorescent nucleic acid stain (dilution 1:1000) and calibrated suspension of polystyrene microspheres (dilution 1:100) at 37° C. for 10 min;
      iii) Performing flow cytometric detection using voltage parameters set at forward scatter—430 units, side scatter—425 units, Fluorescein isothiocyanate—280 units and Phycoerythrin—269 units;
      iv) Determining the density of the bacteria in the sample from the ratio of bacterial signals to microsphere signals in the cytogram;
      v) Calculating the total number of spores as defected by fluorescent nucleic acid staining by the formula $$\text{Total No of spores} = \frac{\text{\# Events in fluorescent nucleic acid stain}^+ \text{ region}}{\text{\# Events in beads}} \times$$
$$10^6 \times \text{dilution factor } (DF);$$

vi) Calculating the number of viable spores by the formula

No of viable spores =
$$\frac{\text{\# Events in } cFDA^+ \text{ region}}{\text{\# Events in beads}} \times 10^6 \times \text{dilution factor } (DF)$$

Or

No of viable spores =
$$\frac{\text{Total spores} - \text{\# Events in } PI^+ \text{ region}}{\text{\# Events in beads}} \times 10^6 \times \text{dilution factor } (DF).$$

2. The method of claim 1, wherein the viability *Bacillus coagulans* MTCC 5856 is tested in probiotic tablets, capsules, dairy products, beverages, confectioneries, cosmeceutical creams, mucosal preparations, and food substances.

* * * * *